(12) United States Patent
Lowry et al.

(10) Patent No.: US 6,509,022 B2
(45) Date of Patent: *Jan. 21, 2003

(54) COMPOSITION FOR USE IN PERSONAL CARE COMPRISING ORGANIC ACID SALTS OF POLYMERIC BIGUANIDINES

(75) Inventors: Michael Richard Lowry, Wirral (GB); Katherine Elizabeth Parker, Leeds (GB)

(73) Assignee: Helene Curtis, Inc., Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/094,324

(22) Filed: Jun. 9, 1998

(65) Prior Publication Data

US 2001/0006647 A1 Jul. 5, 2001

(30) Foreign Application Priority Data

Jun. 13, 1997 (GB) ............................................. 9712317

(51) Int. Cl.⁷ .................................................. A61K 7/00
(52) U.S. Cl. .......................... 424/401; 424/65; 514/564; 514/565; 514/631; 514/634; 514/635
(58) Field of Search .................... 424/401, 65; 514/564, 514/565, 631, 634, 635

(56) References Cited

U.S. PATENT DOCUMENTS

| 4,191,815 A | * | 3/1980 | Jourquin et al. | ............... 521/51 |
| 4,478,821 A | * | 10/1984 | Carillo | ........................ 424/47 |
| 5,268,168 A | * | 12/1993 | Katayama et al. | .......... 424/76.1 |
| 6,010,687 A | | 1/2000 | Cox et al. | ..................... 424/65 |

FOREIGN PATENT DOCUMENTS

| AU | 295256 | | 5/1966 |
| BE | 698595 | | 11/1967 |
| GB | 843676 | | 9/1958 |
| GB | 843676 | * | 8/1960 |
| GB | 1464005 | * | 2/1977 |

* cited by examiner

Primary Examiner—Thurman K. Page
Assistant Examiner—Lakshmi Channavajjala
(74) Attorney, Agent, or Firm—Kevin J. Stein

(57) ABSTRACT

Cosmetic composition for use in personal care applications comprising a carrier and a polymeric biguanide, characterised in that the polymeric biguanide is in the form of its salt with an organic acid containing from 4 to 30 carbon atoms.

16 Claims, No Drawings

COMPOSITION FOR USE IN PERSONAL CARE COMPRISING ORGANIC ACID SALTS OF POLYMERIC BIGUANIDINES

The present invention relates to organic acid salts of polymeric biguanides for use in personal care applications.

Poly(hexamethylenebiguanide) (hereinafter PHMB) has found many uses as a broad spectrum bactericide in both industrial and personal care applications and is commercially available as an aqueous concentrate of its hydrochloride salt. For most applications, the use of PHMB in the form of its hydrochloride salt is eminently suitable. There are, however, some applications where the presence of chloride ion can cause undesirable side effects such as corrosion of metal surfaces. GB 1,464,005 discloses that other salts of PHMB such as sulphate, acetate, gluconate and behenate, may be used as molluscicides. However, no microbiological data are recorded for such salts. Behenic acid is an aliphatic carboxylic acid containing a $C_{21}$-alkyl chain and salts thereof fall within the group of anionic surfactants. The concentrated aqueous solution of PHMB in the form of its hydrochloride salt is clearly stated to be incompatible with anionic surfactants, such as alkyl sulphonates and anionic caramels as disclosed in the Product Information Notes for Vantocil IB (37-8E dated Jun. 1, 1994) and Cosmocil CQ (37-26E dated Apr. 1, 1994). Both Vantocil and Cosmocil are registered trade marks of Zeneca Specialties for PHMB hydrochloride.

Bisbiguanides have also been made available commercially as water-soluble salts such as chlorhexidine (1,1'-hexamethylene bis [5-(4-chlorophenyl)-biguanide] digluconate) and alexidine (1,1'-hexamethylene bis [5(4-(2-ethylhexyl)phenyl)-biguanide]-diacetate). These water-soluble salts and PHMB hydrochloride are not particularly suited to provide a solution of the polymeric biguanide in organic liquids, especially non-polar organic liquids, and do no cause significant corrosion.

It has now been found that PHMB in the form of its salt of an organic acid containing from 4 to 30 carbon atoms exhibits high antimicrobial, especially antibacterial activity, and that such salts exhibit increased solubility in organic media, especially organic liquids.

According to the present invention there is provided a composition comprising a carrier and a polymeric biguanide in the form of its salt with an organic acid containing from 4 to 30 carbon atoms, including mixtures thereof for use in personal care formulations. The polymeric biguanide contains at least one biguanide unit of Formula 1.

Formula 1

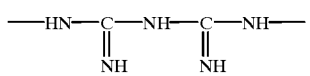

Preferably, the polymeric biguanide contains at least two biguanide units of Formula 1 which are linked by a bridging group which contains at least one methylene group. The bridging group may include a polymethylene chain which may optionally be interrupted by hetero atoms such as oxygen, sulphur or nitrogen. The bridging group may include one or more cyclic nuclei which may be saturated or unsaturated. Preferably, the bridging group is such that there are at least three, and especially at least four, carbon atoms directly interposed between two adjacent biguanide units of Formula 1. Preferably, there are not more than ten and especially not more than eight carbon atoms interposed between two adjacent biguanide units of Formula 1.

The polymeric biguanide may be terminated by a suitable group which may be a hydrocarbyl or substituted hydrocarbyl group or an amine or a group of the formula

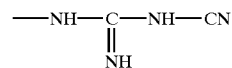

When the terminating group is a hydrocarbyl group, it may be an alkyl, cycloalkyl or aralkyl group.

When the terminating group is a substituted hydrocarbyl group, the substituent may be any substituent which does not exhibit an undesirable adverse effect on the microbiological properties of the polymeric biguanide. Examples of suitable substituents or substituted hydrocarbyl groups are aryloxy, alkoxy, acyl, acyloxy, halogen and nitrile groups or substituents.

When the polymeric biguanide contains two biguanide groups of Formula 1, the two biguanide units are preferably linked by a polymethylene group, especially a hexamethylene group. The terminating group in such polymeric biguanides is preferably 4-chlorophenyl or 2-ethylhexyl. Examples of such compounds are represented by Formulae 2 and 3 in their free base form Formula 2

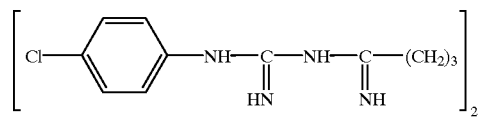

Formula 3

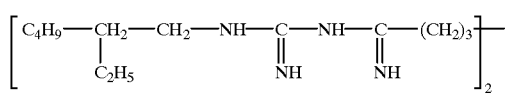

The polymeric biguanide preferably contains more than two biguanide units of Formula 1 and preferably is a linear polymeric biguanide which has a recurring polymeric unit represented by Formula 4

Formula 4

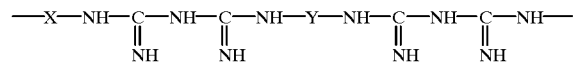

wherein X and Y may be the same or different and represent bridging groups in which, together, the total number of carbon atoms directly interposed between the pairs of nitrogen atoms linking a pair of bridging groups is not less than 9 and not greater than 17.

The bridging groups X and Y may consist of a polymethylene chain, optionally interrupted by a heteroatom such as oxygen, sulphur or nitrogen. X and Y may also incorporate a cyclic nucleus which may be saturated or unsaturated, wherein the number of carbon atoms directly interposed between the pairs of nitrogen atoms linked by X and Y is taken as including that segment of the cyclic group, or groups, which is the shortest. Thus, the number of carbon atoms directly interposed between the nitrogen atoms in the group

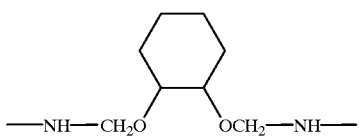

is 4 and not 8.

The preferred polymeric biguanide for use in the present invention is poly(hexamethylenebiguanide), in which both X and Y in Formula 4 are the group —$(CH_2)_6$—.

The polymeric biguanides of Formula 4 are typically obtained as mixtures of polymers in which the polymer chains are of different lengths. Preferably, the number of individual biguanide units

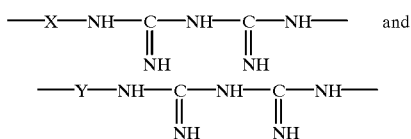

is, together, from 3 to about 80.

In the case of the preferred poly(hexamethylenebiguanide) it is a mixture represented by the compounds of Formula 5 in the free-base form.

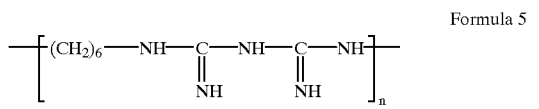

Formula 5 wherein the value of n is from 4 to 40 and especially from 4 to 15. It is particularly preferred that the average value of n in the mixture is 12. Preferably, the average molecular weight of the polymer mixture is from 1100 to 3300.

The organic acid which forms the salt with the polymeric biguanide may contain a phosphonic, phosphoric, sulphonic or sulphuric group but preferably contains a carboxylic acid group. The organic acid may be aromatic but is preferably aliphatic, including alicyclic. When the organic acid is aliphatic, the aliphatic chain of the organic acid may be linear or branched, saturated or unsaturated, including mixtures thereof. Preferably, the aliphatic chain is linear and it is also preferred that the organic acid is an aliphatic carboxylic acid.

It is preferred that the organic acid contains not less than eight, more preferably not less than ten and especially not less than twelve carbon atoms excluding the acid group. Preferably, the organic acid contains not more than 24, more preferably not more than 20 and especially not more than 18 carbon atoms excluding the acid group.

The organic acid may contain more than one acid group but it is preferred that only one such group is present.

The organic acid may be substituted by a halogen or particularly a hydroxy group. It is, however, preferred that the organic acid is free from substituents.

Some aliphatic carboxylic acids are available commercially as mixtures such as those obtained from animal fats and vegetable oils and these contain both staturated and unsaturated aliphatic chains. These have also been found useful, especially the $C_{14-18}$ alkyl carboxylic acids and their fully saturated or hydrogenated analogues.

Examples of optionally substituted carboxylic acids are valeric, hexanoic, octanoic, 2-octanoic, lauric, 5-dodecenoic, myristic, pentadecanoic, palmitic, oleic, stearic, eicosanoic, heptadecanoic, palmitoleic, ricinoleic, 12-hydroxystearic, 16-hydroxyhexadecanoic, 2-hydroxycaproic, 12-hydroxydodecanoic, 5-hydroxydodecanoic, 5-hydroxydecanoic, 4-hydroxydecanoic, dodencanedioic, undecanedioic, sebacic, benzoic, hydroxybenzoic and terephthalic acids.

Particularly useful effects have been obtained when the aliphatic carboxylic acid is stearic acid and the polymeric biguanide is PHMB.

The amount of the polymeric biguanide salts in the composition may vary between wide limits depending on its end usage. Preferably he amount of the polymeric biguanide salts is not less than 1 ppm, more preferably not less than 10 ppm and especially not less than 20 ppm. It will be appreciated that where the composition containing the salt of the polymeric biguanide is to be transported in bulk the amount of the polymeric biguanide salt is as high as possible provided that the biguanide salt remains uniformly distributed throughout the composition. Preferably, the amount of polymeric biguanide salt in the composition is not greater than 30%, more preferably not greater than 25% and especially not greater than 20% based on the total weight of the composition.

The polymeric biguanide salts or compositions thereof according to the invention are for use in personal care formulations. Many of these personal care formulations involve applications to the skin and include, inter alia, hand lotions, foundation creams, emollient creams, facial washing creams, shaving creams, after-shave lotions, sunscreen lotions and creams, sunscreen hair protectors, after-sun lotions, antiperspirants, deodorants, hair gels, hair colorants, hair mousse, mascara, eye shadow, eye liners, lipstick, lip gloss, facial blusher, rouge, foundations and fragrances, shampoo, shampoo gel, rinse conditioning, toothpaste, mouthwash, foam bath liquid, soluble bath oil and liquid soap formulations. Preferably, the amount of polymeric biguanide salt in a personal care formulation is not greater than 2% and more preferably not greater than 1% by weight of the medium. Generally, adequate protection against microbial growth is provided by from 1 ppm to 500 ppm, particularly 10 to 200 ppm and especially 10 to 100 ppm of the polymeric biguanide salt relating to the medium.

Personal care compositions according to the invention may also comprise other materials commonly found in such products. For example, a deodorant product may additionally comprise deodorant/antiperspirant actives, perfumes, preservatives and antioxidants, emollients etc.

Examples of other ingredients which can optionally be present in the composition according to the invention include:

emollients, such as non-volatile silicones, hydrocarbons or mineral oils.

Non-volatile silicones include polydimethylsiloxane having a viscosity in excess of 5 $mm^2s^{-1}$, for example, from 50 to 1000 $mm^2s^{-1}$, such as DOW CORNING 200 Fluids (standard viscosities 50–1000 $mm^2s^{-1}$).

Other useful emollients include PEG-400 distearate, and ethylene oxide and/or propylene oxide condensation products having the following formula:

$$RO\ (C_2H_4O)_a(C_3H_6O)_bH$$

where R is either hydrogen or a hydrocarbon chain having from about 2 to 20 carbon atoms, and a and b are each from about 0 to 35 and a+b is from about 5 to 35. An example of such an emollient is Fluid AP, a condensate of about 14 moles of propylene oxide with about 1 mole of butyl alcohol sold by Union Carbide.

Still further emollients suitable for use in the present solid stick compositions include fatty acid and fatty alcohol esters and water insoluble ethers.

- thickeners, such as clays, for example Bentone 38; and silica, for example Aerosil 200;
- skin feel improvers, such as talc and finely divided polyethylene, an example of which is ACUMIST B18;
- cosmetically acceptable vehicles, such as anhydrous ethanol and other emollients;
- perfumes;
- preservatives; and
- other cosmetic adjuncts conventionally employed in personal care formulations.

A preferred optional component in solid products according to the invention, includes a wax such as castor wax, Synchrowax HRC, carnauba wax, beeswax, silicone waxes and glycerol monostearate and mixture thereof at levels of from about 1 to 10% preferably 2 to 8% by weight. If present, the wax is believed to enhance structural stability of the composition in the molten state.

The ingredients which can optionally be present in the composition can conveniently form the balance of the composition.

The invention is illustrated by the following examples wherein all parts and percentages are references to weight unless indicated to the contrary.

EXAMPLE 1

Preparation of stearate of PHMB

Water (150 liters) was added to a reactor vessel followed by stearic acid (14.8 kg, 0.047M). Sodium hydroxide flake (1.88 kg, 0.047M) was added with stirring, giving a pH value in the range 9.0 to 10.0. PHMB hydrochloride (50 liters as 20% aqueous solution, 0.047M, Vantocil IB ex. Zeneca) was added and the reactants stirred at 80° C. for 2 hours. After cooling, the PHMB stearate salt was separated on a slurry filter, washed with water and dried.

The product was obtained as a paste containing 11.0 kg PHMB stearate (50% theoretical).

The PHMB stearate salt exhibited similar microbiological activity to the hydrochloride salt when allowance is made for the different molecular weights.

EXAMPLE 2

The following example is a deodorant aerosol formulation comprising the stearate salt of formula 1 where the average value of n is 12. The formulation is made by methods common in the art.

|  | % by weight |
| --- | --- |
| Ethanol | 57.45 |
| Propellant (CAP 40) | 40 |
| PHMB stearate (n = 12) | 0.05 |
| Perfume | 1.5 |
| Emollient (Isopropyl myristate) | 1.0 |

EXAMPLE 3

The following is a typical liquid detergent composition prepared by conventional methods:

| Ingredient | % by weight |
| --- | --- |
| SLES 3 EO (1) | 10 |
| CAPB (2) | 10 |
| Glycerol | 5 |
| PEG 600 | 5 |
| PEG-80 glycerol tallowate | 3 |
| Propane-1,2-diol | 3 |
| Clay (3) | 0.6 |
| PHMB (n = 12) stearate | 0.05 |
| Water | to 100 |

(1) Sodium lauryl ether sulphate (3EO) ex Henkel
(2) Cocoamidopropyl betaine ex Henkel
(3) Laponite XLS ex Laporte

What is claimed is:

1. Cosmetic composition for use in personal care applications comprising:
   (a) an organic medium; and
   (b) a polymeric biguanide,
wherein the polymeric biguanide contains more than two biguanide units of the formula

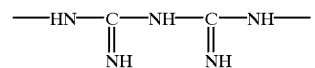

and is in the form of its salt with an organic acid containing from 4 to 30 carbon atoms, including mixtures thereof.

2. Composition according to claim 1 wherein the polymeric biguanide is a linear polymeric biguanide which has a recurring polymeric unit represented by the formula

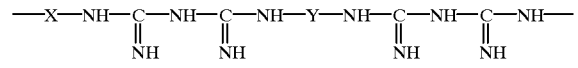

wherein X and Y may be the same or different and represent bridging groups in which, together, the total number of carbon atoms directly interposed between the pairs of nitrogen atoms linked by X and Y is not less than 9 and not more than 17.

3. Composition according to claim 2 wherein both X and Y are a hexamethylene group.

4. Composition according to claim 1 wherein the polymeric biguanide is a mixture represented by the compounds in the free-base form of the formula

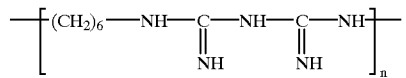

wherein the average value for n ranges from 4 to 40.

5. Composition according to claim 4 wherein the average value for n ranges from 4 to 15.

6. Composition according to claim 4 wherein the average value for n is 12.

7. Composition as claimed in claim 1 wherein the organic acid is selected from the group consisting of valeric, hexanoic, octanoic, 2-octanoic, lauric, 5-dodecenoic, myristic, pentadecanoic, palmitic, oleic, stearic, eicosanoic, heptadecanoic, palmitoleic, ricinoleic, 12-hydroxystearic, 16-hydroxyhexadecanoic, 2-hydroxycaproic, 12-hydroxydodecanoic, 5-hydroxydodecanoic, 5-hydroxydecanoic, 4-hydroxydecanoic, dodecanedioic, undecanedioic, sebacic, benzoic, hydroxybenzoic and terephthalic acids.

8. Composition as claimed in claim 1 wherein the organic acid contains from 12 to 18 carbon atoms.

9. Composition according to claim 1 wherein the organic acid is stearic acid.

10. Composition according to claim 1 wherein the composition is a deodorant composition.

11. Composition according to claim 1 wherein the composition is an antiperspirant composition.

12. A personal care formulation comprising as an antimicrobial agent a polymeric biguanide of claim 1.

13. A method for reducing or eliminating malodor which comprises administering to the skin an effective amount of a composition according to claim 1.

14. Cosmetic composition for use in personal care applications consisting essentially of:

(a) an organic medium; and
   (b) a polymeric biguanide;

wherein the polymeric biguanide contains more than two biguanide units of the formula

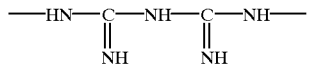

and is in the form of its salt with an organic acid containing from 4 to 30 carbon atoms.

15. An antiperspirant composition consisting essentially of:

(a) an organic carrier;
   (b) a polymeric biguanide comprising more than two biguanide units of

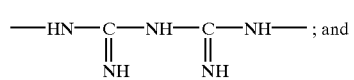

Formula I (c) a surfactant;

wherein the polymeric biguanide is in the form of its salt with an organic acid containing from 4 to 30 carbon atoms.

16. Cosmetic composition for use in personal care applications comprising:

(a) an organic medium; and
   (b) a polymeric biguanide, and
   (c) an emollient, where the polymeric biguanide contains more than two biguanide units of the formula

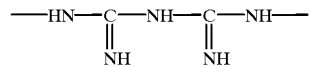

and is in the form of its salt with an organic acid containing from 4 to 30 carbon atoms, including mixtures thereof.

* * * * *